United States Patent [19]

Van Meter et al.

[11] Patent Number: 5,513,517
[45] Date of Patent: May 7, 1996

[54] ROTOR-STATOR ADAPTER FOR SENSITIVE ROTATING VISCOMETERS

[75] Inventors: John J. Van Meter; Kevin J. Wolfe; Robert H. Seer; Gregory C. Müller, all of Midland, Mich.

[73] Assignee: Tannas Co., Midland, Mich.

[21] Appl. No.: 308,918

[22] Filed: Sep. 20, 1994

[51] Int. Cl.[6] ................................................. G01N 11/14
[52] U.S. Cl. ............................ 73/54.280; 73/54.350; 279/2.030
[58] Field of Search ....................... 73/54.28, 54.29, 73/54.31, 54.32, 54.33, 54.34, 54.35

[56] References Cited

U.S. PATENT DOCUMENTS

| | | | |
|---|---|---|---|
| 122,426 | 1/1872 | Andrew | 403/314 |
| 453,622 | 6/1891 | Cheney | 403/290 X |
| 668,017 | 2/1901 | Pessano | 403/308 |
| 724,475 | 4/1903 | Hilmo | 403/290 X |
| 817,588 | 4/1906 | Reising | 403/310 |
| 904,341 | 11/1908 | Lindstrom . | |
| 1,251,464 | 1/1918 | Becker . | |
| 1,321,264 | 11/1919 | Wagner et al. | 403/300 |
| 2,056,248 | 10/1936 | Buchanan | 173/303 |
| 2,160,694 | 5/1939 | Buchanan | 287/75 |
| 3,359,528 | 12/1967 | Scholz | 339/65 |
| 3,518,748 | 7/1970 | Howlett | 29/452 |
| 3,810,078 | 5/1974 | Chordas | 339/268 R |
| 4,441,837 | 4/1984 | Mastroni | 403/300 |
| 4,524,484 | 6/1985 | Graham | 16/115 |
| 4,623,277 | 11/1986 | Wayne et al. | 403/314 |
| 4,645,473 | 2/1987 | Mochizuki | 464/79 |
| 4,648,263 | 3/1987 | Deysarkar et al. | 73/59 |
| 5,004,367 | 4/1991 | Wood, Jr. | 403/36 |
| 5,369,988 | 12/1994 | Selby | 73/54.28 |

OTHER PUBLICATIONS

ASTM Designation: D 5133—90 (1990).

*Primary Examiner*—Hezron E. Williams
*Assistant Examiner*—Jay L. Politzer
*Attorney, Agent, or Firm*—Christopher John Rudy

[57] ABSTRACT

A wall in a lower portion of a hollow support member having an open upper end and upper interior surface and a lower interior cylindrical surface to encircle and retain the stator of a rotating viscometer such as a Brookfield viscometer is provided with external threads and is slotted. A corresponding nut threads thereon and applies pressure to hold the stator of the viscometer.

24 Claims, 3 Drawing Sheets

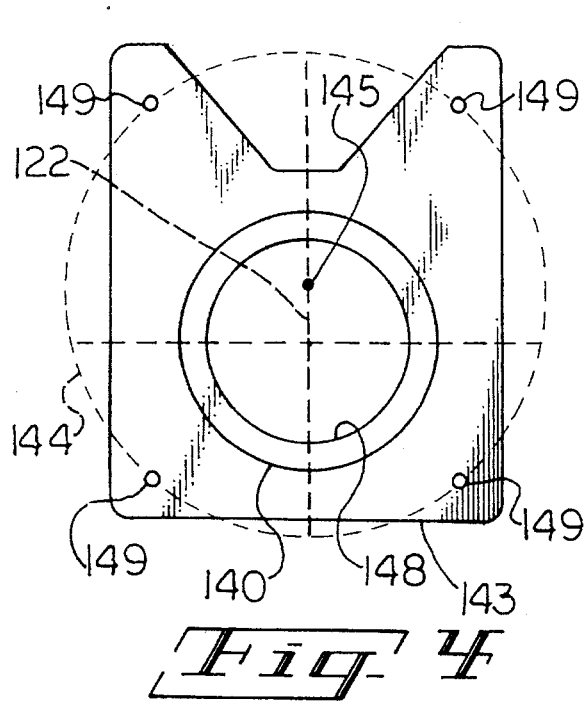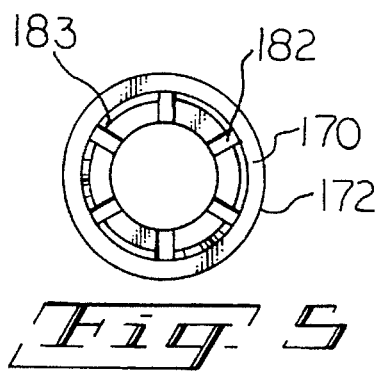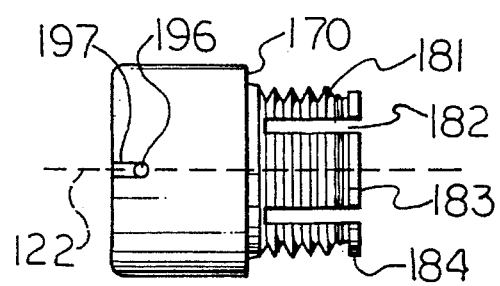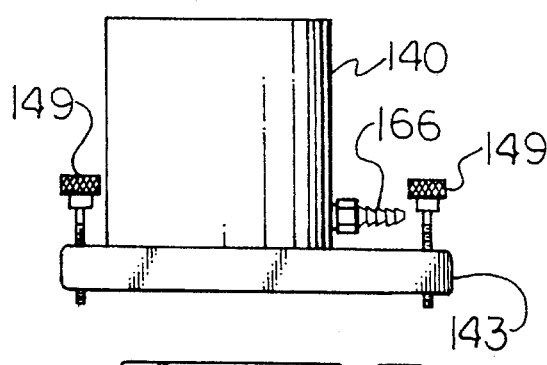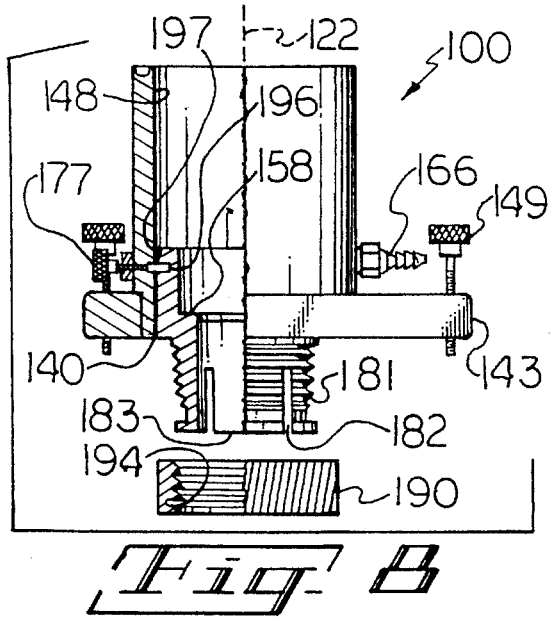

ROTOR-STATOR ADAPTER FOR SENSITIVE ROTATING VISCOMETERS

FIELD

In general, the present invention concerns rotating viscometers, useful in measuring viscosities of liquids. More particularly, it concerns attachments for centering and supporting various rotational and static parts of the viscometer.

BACKGROUND

Rotational viscometers require a rotating element called the rotor and a stationary element in fluid contact with the rotor which stationary element is called the stator. Most often the rotor turns within the stator. Sensitive rotatational viscometers such as the Brookfield viscometer are well-known instruments for measuring viscosities of liquids. Usually, the rotor, which is driven by the Brookfield head, is immersed in a large container of liquid in which the walls of the container are at some considerable distance from the rotor and thus have little influence on the measurement of the viscous value. However, in some applications such as in the well-known Scanning Brookfield Technique used in ASTM D 5133, incorporated herein by reference as its 1990 version, the rotor must be relatively close to the stator wall to gain the necessary sensitivity. In such a case, the rotor must be centered very carefully.

This Scanning Brookfield Technique, discovered and developed by Mr. Theodore W. Selby and licensed to the Tannas Co., Midland, Mich., was improved by a support and centering device disclosed by Deysarkar et al., U.S. Pat. No. 4,648,263 (Mar. 10, 1987), incorporated herein by reference.

In practice, problems are encountered with the comercially available support and centering attachment as of Deysarkar et al., which is known commercially as the Pennzoil/Tannas rotor/stator centering adapter, Tannas Model Number SBV-P. In particular, and in reference to the foregoing patent, in a centering device 40 for sensitive rotating viscometer 10 having a cylindrical lower end of pivot housing 20 and rotor 24, particularly in the Model Number SBV-P adapter, an O-ring 00, present in the SBV-P adapter in a slot cut in interior surface 54 of cylindrical member 70, can swell as from contact with solvents or oil to the point where sometimes, upon the contraction of the constraining cylindrical member 70, a glass stator 28 may break. The O-ring also may become worn or oily, and, if a loose fit between cylindrical member 70 and stator 28 is engendered, slippage and rotation of the stator occurs during testing which destroys the value of the test. Furthermore, the O-ring can be difficult to install and remove for replacement. Another effect of low-temperature contraction of cylindrical member 70 is that when bath 44 controls the temperature of test liquid 26 at minus 40 degrees C., or below, separation of parts of device 40, to include removal of a glass stator 28, which has annular lip 56, the stator being filled with tested liquid, from the lower end 52 of the device, becomes very difficult because of the aforementioned contraction of the engineering thermoplastic employed to make the adapter. Other problems exist.

What is needed is an adapter which overcomes such problems while providing for precise centering of the rotor spindle in the stator of a sensitive rotating viscometer. The adapter should be readily manufacturable—and be efficient to operate, especially by even inexperienced operators.

SUMMARY

The present invention provides for, especially in a device for supporting a sensitive viscometer above a cylindrical stator containing a predetermined quantity of fluid, the fluid having a viscosity, the viscosity of the fluid being measured by a viscometer with a cylindrical rotor suspended from a pivot housing fixed to a lower end of the viscometer and centered within the fluid by the device, the rotor being rotatable about its longitudinal axis by the viscometer and cooperating with the stator and fluid to create drag related to the viscosity, the device having a hollow support member having an open upper end and upper interior surface shaped to correspond and snugly engage an exterior surface of the pivot housing, the viscometer projecting upwardly from substantially an upper end of the support member, first means for retaining the pivot housing in stationary position and snug contact with the upper interior surface, the support member further including a lower interior cylindrical surface in snug contact with an exterior cylindrical surface of the stator, and second means for retaining the stator in stationary position and snug contact with the lower cylindrical surface, the upper and lower surfaces being coaxial with each other to substantially precisely center the rotor within the stator, an improvement which comprises:

an externally threaded wall in a lower portion of the support member, which threaded wall is perforately slotted, the wall having means to accept pressure and direct it inwardly, and a correspondingly, internally threaded nut for attachment about the threaded, slotted wall by threading, the nut having means to exert guiding pressure on the means to accept pressure of the wall so as to cause it to be directed inwardly by tightening of the nut so as to cause the snug contact between the lower interior surface of the support member and the exterior cylindrical surface of the stator.

The invention is useful in measuring viscosities with sensitive rotating viscometers, especially Brookfield viscometers.

Significantly, by the invention, problems of the prior art such as aforesaid are ameliorated or eliminated. The adapter hereof provides for precise centering of the rotor spindle in the stator of a sensitive rotating viscometer. Moreover, the article of the invention is readily made—and is easily and effectively used, especially to include by even inexperienced operators. Numerous further advantages attend the invention.

DRAWINGS IN BRIEF

The drawings form part of the specification hereof.

In the present drawings, in which like numerals refer to like features, note:

FIG. 4 is a top view of a collar housing of the invention.

FIG. 5 is a bottom view of a stator collar as within FIG. 1.

FIG. 6 is a side view of the stator collar of FIG. 3.

FIG. 7 is a side view of the collar housing of FIG. 2.

FIG. 8 is a partial cross-sectional view of an adapter hereof as within FIGS. 1 & 2.

ILLUSTRATIVE DETAIL

Figure 1:
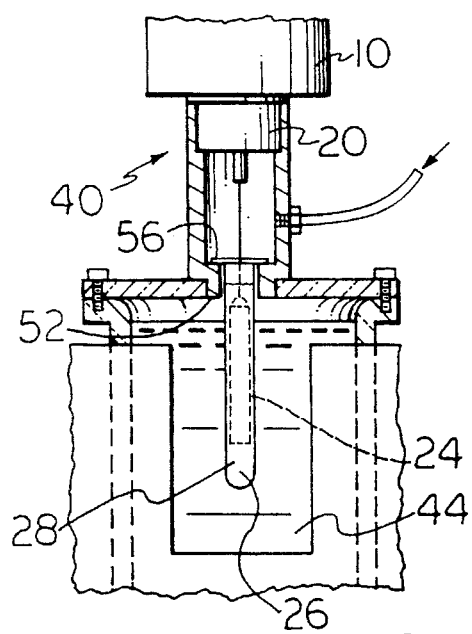
FIG. 1 is a cross-sectional view of a support and centering device of the prior art, from the '263 patent to Deysarkar et al.
Figure 2:
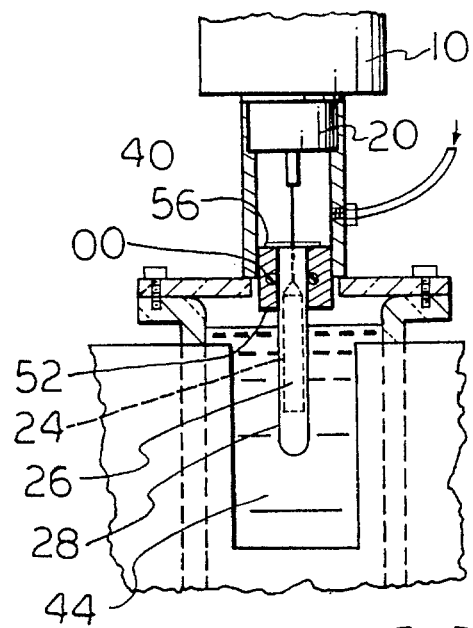
FIG. 2 is a cross-sectional view similar to FIG. 1, showing a preferred embodiment from the '263 patent to Deysarkar et al.
Figure 3:
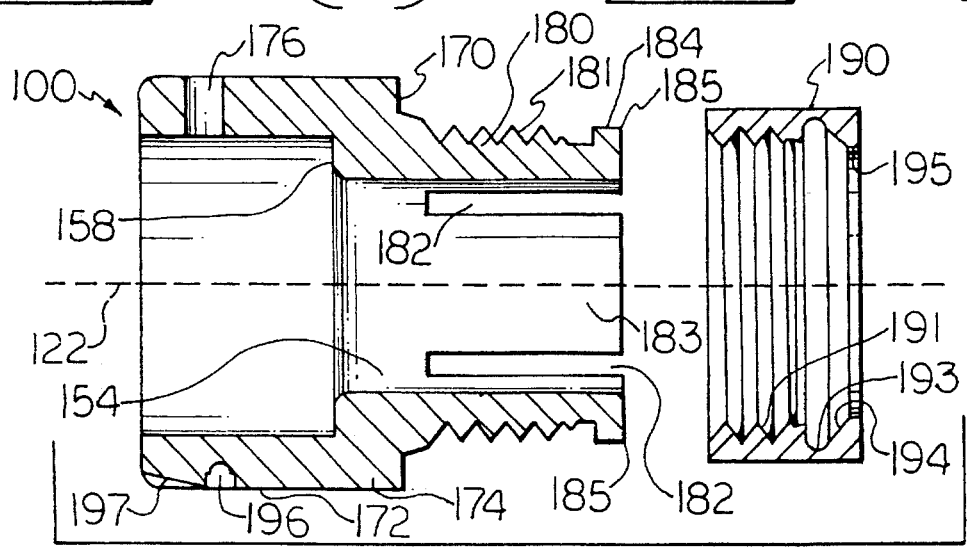
FIG. 3 is an exploded, partial cross-sectional view including a lower portion of an adapter stator collar and nut of the invention.
Figure 9:
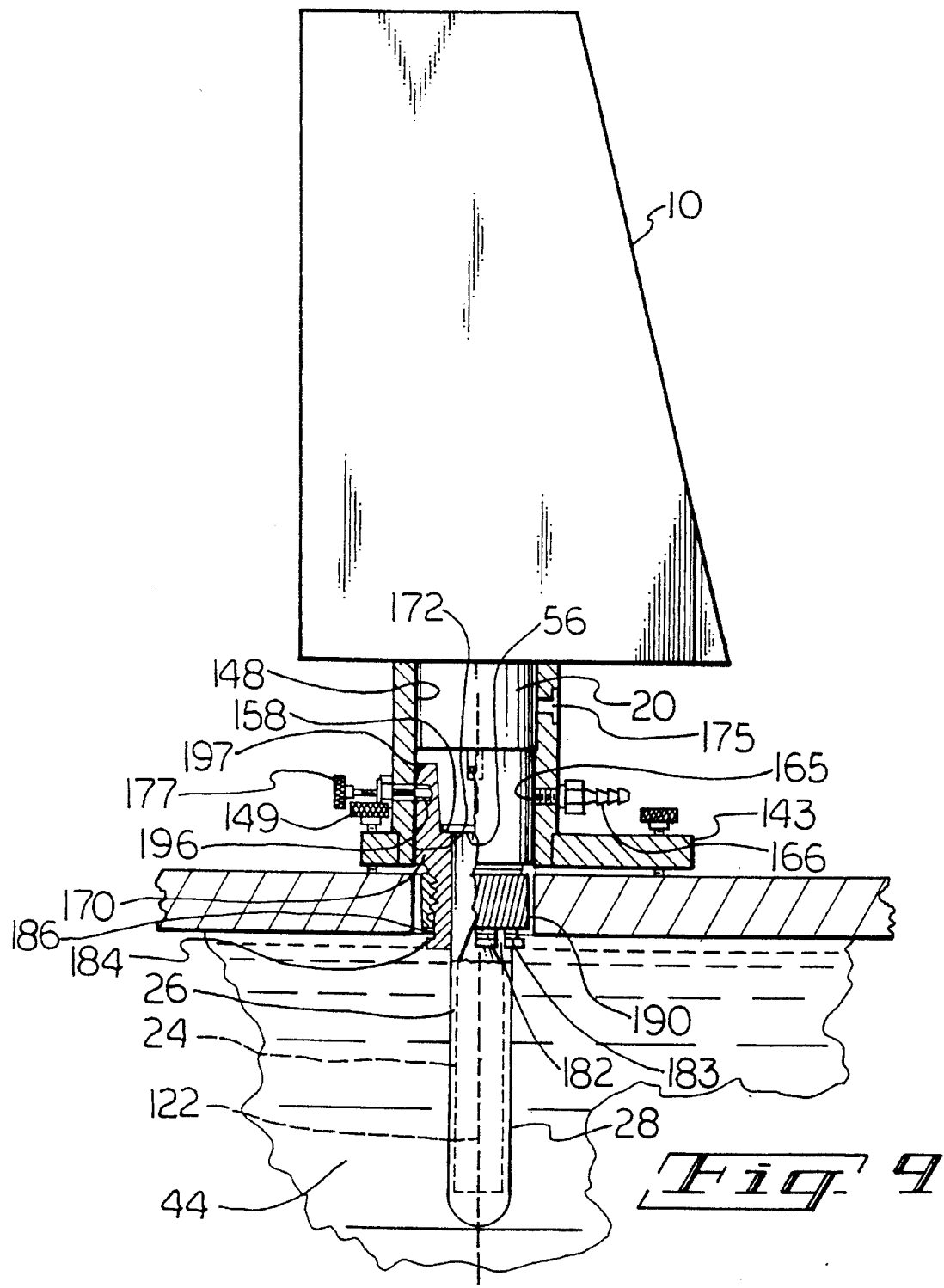
FIG. 9 is a partial cross-sectional view of an adapter hereof, in assembly with a Brookfield viscometer to include among other components a stator.

In reference to the drawings, adaptor 100 has a wall 180 which is eternally threaded 181 in a lower portion of support member assembly 140. The threaded wall is perforately slotted 182 so as to provide by each slot an opening from the exterior to the interior of the wall and preferably thus form fingers 183 from a plurality of axially-directed slots. The wall has a means to accept pressure and direct it inwardly such as, for example, may be provided by suitably tapered threads, or other surfaces, which may include protrusions, for example, a nut retaining lip 183 on the stator collar, which may be squared, rounded or beveled at its lower, distal end 184, capable of receiving the pressure and to have it directed inwardly. Such a pressure-receiving protrusion can be provided by a first, lower thread from among threads 181. As well, the adapter has a nut 190 which is correspondingly, internally threaded 191 for attachment by threading about the threaded, slotted wall 180. The nut has means to exert guiding pressure on the means to accept pressure of the wall so as to cause it to be directed inwardly by tightening of the nut such as, for example, may be provided by suitably reverse tapered threads, or other surfaces, which may include ramps or other suitable protrusions such as an internal reverse bevel 194. This causes the snug contact between the lower interior surface 154 of the support member and the exterior cylindrical surface of the stator 28.

In the stator collar 170, an external radial recess may be present for receiving a protrusion 185 of the nut. In the nut 190, an internal radial recess 193 may be present for receiving the protrusion 184 of the stator collar. Such keeps the nut on the adapter assembly, advantageous in set-up and take-down during test runs. Should the nut become loosened thus, it will not fall off the assembly, say, into the bath reservoir or get lost.

Preferably, the adapter is basically of three major pieces: collar housing 140; stator collar 170; and the nut 190. The collar housing with its internal surface 148 snugly embraces the stator collar about an upper portion 172 of its outside surface 174. Inner cylindrical surface 154 of the stator collar is dimensioned to receive and encircle an upper end of the stator 28.

Preferably, the three major pieces of the adapter are generally cylindrical. As well thus, they are concentric with respect to the longitudinal axis of the adapter.

Perfect centering of a Brookfield viscometer rotor 24 within the stator 28 is achieved by simply slipping the stator through the upper end of the stator collar until stator annular lip 56 contacts upwardly-directed stop surface 158 found above surface 154, which is followed by tightening the nut and insertion of the stator, nut and stator collar assembly into the collar housing. Internal dimensions of the collar housing are such that they receive and encircle the stator collar snugly.

In addition, pin 177 in the collar housing may provide vertical fastening of the collar housing to the stator collar. The pin, for example, which may be a spring-plunger, may rest in plunger hole 196 of the stator collar, first riding up plunger hole ramp 197 as the stator collar assembly is inserted into the collar housing.

The adapter 100 can advantageously facilitate introduction of an inert gas blanket, to preferably include a low-moisture gas, over the test sample liquid 26 in the stator 28 by allowing injection of the gas into the interior of the adapter through porthole 165 as by means of a fitting 166 and through porthole 176 in the stator collar. Vent 175 may be provided to prevent a pressure build-up of gas within the interior region.

Plate 143 may be present on the collar housing. Leveling of the plate is easily and reliably accomplished as is well-known in the art. Preferably, the plate 143 extends laterally a distance necessary to and provide support and balance for the adapter assembly supporting a viscometer 10 having a with a cylindrical lower end of pivot housing 20 and rotor 24 such as a Scanning Digital Brookfield Viscometer which has a heavy, offset head.

Means for adjusting 149 for leveling the viscometer head attached to the adapter assembly 100 are positioned on the circumference of an imaginary ellipse 144 inside of which the axis of rotation 122 of the rotor is bounded. Preferably, the means for adjusting are the four level adjusting screws 149 shown which are substantially equidistant from the center 145 of the imaginary ellipse 144 which has a major axis intersecting the axis of rotation 122, and preferably, the center 145 of imaginary ellipse 144 does not lie on the axis of rotation 122.

The adapter is made of any suitable material. Advantageously, it is made of a thermally-insulating engineering material to include engineering thermoset resins and engineering thermoplastics such as homo- or co-polymeric acetal resins, which may be injection molded and/or machined to the required dimensions and tolerances. For example, DELRIN acetal homopolymer (The Polymer Corp., Reading, Pa.) may be thus molded and machined to produce adapter components hereof.

CONCLUSION

The present invention is thus provided. Numerous modifications can be effected by those skilled in the art in the spirit of the invention, the lateral claim scope of which is particularly pointed out as follows:

We claim:

1. In a device useful for supporting a sensitive viscometer above a cylindrical stator containing a predetermined quantity of fluid, the fluid having a viscosity, the viscosity of the fluid being measured by the viscometer with a cylindrical rotor suspended from a pivot housing fixed to a lower end of the viscometer and centered within the fluid by the device, the rotor being rotatable about its longitudinal axis by the viscometer and cooperating with the stator and fluid to create drag related to the viscosity, the device having a hollow support member having an open upper end and upper interior surface shaped to correspond and snugly engage an exterior surface of the pivot housing, the viscometer projecting upwardly from substantially an upper end of the support member, first means for retaining the pivot housing in stationary position and snug contact with the upper interior surface, the support member further including a lower interior cylindrical surface in snug contact with an exterior cylindrical surface of the stator, and second means for retaining the stator in stationary position and snug contact with the lower cylindrical surface, the upper and lower surfaces being coaxial with each other to center the rotor within the stator, an improvement in the device which comprises a rotor-stator adapter for sensitive rotating viscometers, containing:

an externally threaded wall in a lower portion of the support member, which threaded wall is perforately slotted, the wall having means to accept pressure and direct it inwardly, and a correspondingly, internally threaded nut for attachment about the threaded, slotted wall by threading, the nut having means to exert guiding pressure on the means to accept pressure of the wall so as to cause it to be directed inwardly by tightening of the nut so as to cause the snug contact between the lower interior surface of the support member and the exterior cylindrical surface of the stator.

2. The adapter of claim 1, wherein the second means includes a stop defining an upwardly directed nesting surface, upon which an annular lip of the stator can rest.

3. The adapter of claim 1, wherein three major pieces are present: a collar housing; a stator collar; and the nut.

4. The adapter of claim 2, wherein three major pieces are present: a collar housing; a stator collar; and the nut.

5. The adapter of claim 3, wherein a plurality of slots are present to form a plurality of fingers in the lower portion of the support member stator collar.

6. The adapter of claim 4, wherein a plurality of slots are present to form a plurality of fingers in the lower portion of the support member stator collar.

7. The adapter of claim 5, wherein the support collar has an external, radially directed protrusion at its lower, distal end, and the nut has a recess to receive it.

8. The adapter of claim 6, wherein the support collar has an external, radially directed protrusion at its lower, distal end, and the nut has a recess to receive it.

9. The adapter of claim 7, wherein the nut has an internal protrusion at its lower end, and the support collar has has a radial recess on an external surface to receive it.

10. The adapter of claim 8, wherein the nut has an internal protrusion at its lower end, and the support collar has a radial recess on an external surface to receive it.

11. The adapter of claim 9, which is generally made of a thermally-insulating engineering material.

12. The adapter of claim 10, which is generally made of a thermally-insulating engineering material.

13. The adapter of claim 9, which has spring plunger pin in the collar housing to provide vertical fastening of the collar housing to the stator collar, and which pin can rest in a plunger hole of the stator collar, which stator collar has a plunger hole ramp for the pin to ride up on on insertion of the stator collar into the collar housing.

14. The adapter of claim 10, which has spring plunger pin in the collar housing to provide vertical fastening of the collar housing to the stator collar, and which pin can rest in a plunger hole of the stator collar, which stator collar has a plunger hole ramp for the pin to ride up on on insertion of the stator collar into the collar housing.

15. The adapter of claim 9, which has a porthole and fitting in the collar housing for injection of a gas into interior regions of the adapter, a porthole in the stator collar through which injected gas can pass through, and a vent in the collar housing for the gas.

16. The adapter of claim 10, which has a porthole and fitting in the collar housing for injection of a gas into interior regions of the adapter, a porthole in the stator collar through which injected gas can pass through, and a vent in the collar housing for the gas.

17. A collar housing useful in supporting a sensitive viscometer above a cylindrical stator containing a predetermined quantity of fluid having a viscosity which is measurable by the viscometer with a cylindrical rotor suspended from a pivot housing fixed to a lower end of the viscometer and centered within the fluid on an axis of rotation of the rotor by a stator collar and the collar housing snugly engaged, comprising a hollow support member having an open upper end and upper interior surface shaped to correspond and snugly engage an exterior surface of the pivot housing such that the viscometer can project upwardly from substantially an upper end of the support member in the fashion of a head; an open lower end and lower interior surface shaped to correspond and snugly engage an exterior surface of the stator collar in communication with the open upper end, and an noncircular plate laterally, outwardly extending from the lower end of the hollow support member having adjusting means for leveling the viscometer head attached to the upper end of the hollow support member through which an imaginary ellipse having a circumference passes, which adjusting means are positioned on the circumference of an imaginary ellipse inside of which the axis of rotation of the rotor is bounded, wherein the imaginary ellipse has a major axis intersecting the axis of rotation.

18. The collar housing of claim 17, wherein the adjusting means are four screws substantially equidistant from the center of the imaginary ellipse, and the center of the imaginary ellipse does not lie on the axis of rotation of the rotor.

19. The collar housing of claim 18, wherein said plate has a generally rectangular profile when taken from a top view.

20. The collar housing of claim 19, wherein there is a notch in the generally rectangular profile.

21. An assembly comprising a generally cylindrical, hollow collar having an upper portion having a wall with cylindrical inside and outside surfaces; a lower portion having a wall with a cylindrical inside surface and an external surface having male threads, wherein the lower wall has a plurality of axially-directed slots to form fingers therein, wherein a lip is present on the lower wall external surface at a lower, distal end of the lower wall, and wherein the upper inside surface has a greater diameter than the lower inside surface; an upwardly-directed stop surface above the lower inside surface and below the upper inside surface; and in the lower wall a means to accept pressure and direct it inwardly; and a nut having inside and outside surfaces, having female threads on the inside surface corresponding to the male threads on the external surface of the lower wall of the hollow collar, an internal, radial recess for receiving the lip of the collar, and a means to exert guiding pressure on the means to accept pressure of the lower wall of the collar so as to cause the lower wall of the collar to be directed inwardly by tightening of the nut on the collar.

22. The assembly of claim 21, wherein the means to accept pressure in the lower wall of the collar is provided by the lip thereof; the means to exert guiding pressure is provided by a protrusion on the inside surface of the lower wall distal to the the internal, radial recess of the nut; and a hole is present in the upper portion wall.

23. The assembly of claim 21, which is made of a thermally-insulating, engineering material.

24. The assembly of claim 22, which is made of a thermally-insulating, engineering material.

* * * * *

UNITED STATES PATENT AND TRADEMARK OFFICE
CERTIFICATE OF CORRECTION

PATENT NO. : 5,513,517
DATED : May 7, 1996
INVENTOR(S) : Van Meter et al.

It is certified that error appears in the above-indentified patent and that said Letters Patent is hereby corrected as shown below:

On the title page, item [75] in the list of inventors,
delete "John J. Van Meter;" and insert therefor
-- John L. Van Meter; --.

In column 2, line 6, after "by" delete "a" and insert therefor -- the --.

In column 3, line 12, delete "adaptor" and insert therefor -- adapter --.

In column 4, line 16, delete "having a" entirely.

In column 4, line 45, delete "lateral" and insert therefor -- literal --.

In claim 17, column 6, line 17, delete "an" and insert therefor -- a --.

Signed and Sealed this

Sixteenth Day of July, 1996

Attest:

BRUCE LEHMAN

Attesting Officer

Commissioner of Patents and Trademarks